United States Patent [19]

Kwantes et al.

[11] 4,308,404
[45] Dec. 29, 1981

[54] PREPARATION OF BISPHENOLS

[75] Inventors: Ariën Kwantes; Arie Van Dongen; Hendrik A. C. Groeneveld, all of Amsterdam, Netherlands

[73] Assignee: Shell Oil Company, Houston, Tex.

[21] Appl. No.: 922,021

[22] Filed: Jul. 5, 1978

[30] Foreign Application Priority Data

Jul. 11, 1977 [GB] United Kingdom ............... 29012/77

[51] Int. Cl.³ ............................................. C07C 39/16
[52] U.S. Cl. ..................................... 568/727; 568/728
[58] Field of Search ................................. 568/727, 728

[56] References Cited

U.S. PATENT DOCUMENTS

| 2,730,552 | 1/1956 | Williamson | 568/727 |
| 2,775,620 | 12/1956 | Williamson | 568/727 |
| 2,791,616 | 5/1957 | Luten | 568/727 |
| 3,242,220 | 3/1966 | Apel et al. | 568/727 |

Primary Examiner—Werren B. Lone

[57] ABSTRACT

An improved continuous process for preparing bisphenols from phenols and carbonyl compounds in the presence of an acidic ion-exchange resin is described wherein the reaction zone comprises at least two reactors in series and a part the effluent from at least one reactor, with the exception of the last reactor, is recycled.

8 Claims, 1 Drawing Figure

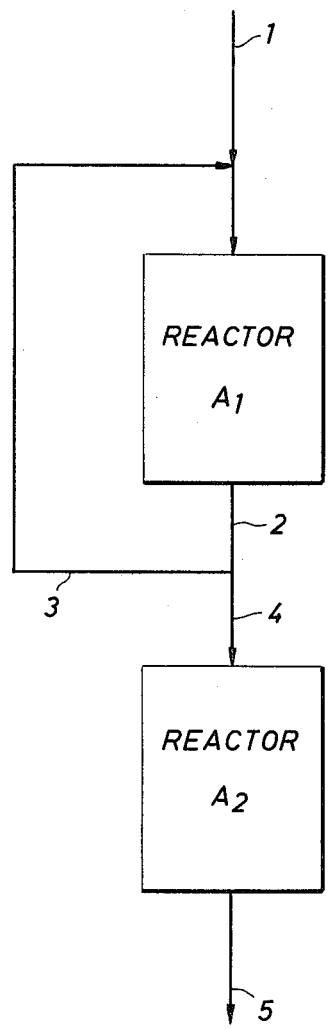

PREPARATION OF BISPHENOLS

BACKGROUND OF THE INVENTION

The invention is concerned with a process for the preparation of bisphenols and with the bisphenols so prepared.

It is known to prepare bisphenols, e.g., Bisphenol A, by continually rejecting at least 2 moles of a phenol with a carbonyl compound in the presence of an acidic ion-exchange resin in a reaction zone comprising at least two reactors in series and to recover the bisphenol from the effluent from the last reactor, e.g., see U.K. patent No. 883,391. One problem of such a process is that the activity of the resin, especially in the first reactor, decreases with an increasing number of run hours.

It has now surprisingly been found that the activity of the resin does not decrease to any substantial extent if a part of at least one reactor effluent, with the exception of the last reactor effluent, is recycled, preferably to the first reactor.

SUMMARY OF THE INVENTION

The present invention is directed to an improved continuous process for preparing bisphenols from phenols and carbonyl compounds in the presence of an acidic ion-exchange resin wherein the process is performed in a reaction zone comprising at least two reactors in series and wherein at least a part of the effluent from at least one reactor is recycled to a prior reactor.

DESCRIPTION OF THE DRAWINGS

The drawing is a schematic design of a preferred embodiment of the present process utilizing two reactors in series.

DESCRIPTION OF THE PREFERRED EMBODIMENT

Accordingly, the present invention is concerned with a continuous process for the preparation of bisphenols comprising reacting at least two moles of a phenol with a carbonyl compound in the presence of an acidic ion-exchange resin in a reaction zone comprising at least two reactors in series and recovering the bisphenol from the effluent from the last reactor, characterized in that a part of the effluent from at least one reactor, with the exception of the last reactor, is recycled, preferably to at least the first reactor.

In a preferred embodiment of the present invention the recycle ratio, which is the ratio, by weight, of the recycle stream to the stream fed to the following reactor is in the range of from 0.1:; to 10:1 preferably from 0.3:1 to 3:1.

Suitably the volume of the first reactor is from 5 to 70% of the volume of the reaction zone and preferably the reaction zone comprises two reactors. Suitably all of the phenol is fed to the first reactor and the carbonyl compound is either fed all to the first reactor or divided between the first reactor and the second and possibly further reactors, if any.

The bisphenol may be recovered from the effluent from the last reactor by conventional techniques such as by the removal of the unreacted carbonyl compound, water and a part of the phenol by distillation followed by the removal of the remaining phenol by evaporation. Techniques, such as crystallization, may also be used.

Suitable acidic ion-exchange resins for use in the present invention are those whose structure is such as to render the resin insoluble in the reaction medium. Preferred resins contain a plurality of sulphonic acid groups. Such sulphonated ion-exchange resins may be sulphonated styrene-divinylbenzene copolymers or sulphonated phenolformaldehyde resins. The sulphonated resins are commercially available in a dry or water-swollen form and either form may be used in the process. Specific examples of suitable resins are Amberlite IR-120H, Amberlite 200, Amberlyst 15H⊕, Dowex 50-X-4, Dowex MSC-1H, Duolite C-26, Permuit QH, Chempro C-20 and Imac C8P/H+ (Amberlite, Amberlyst, Dowex, Duolite, Permutit, Chempro and Imac are registered Trade Marks). The exchange capacity of the acidic resin is preferably at least 2.0 meq H+/g of dry resin, with exchange capacities in the range of from 3.0 to 5.5 meq H+/g of dry resin being particularly preferred.

The acidic ion-exchange resin may be partially modified with a compound having an acidic reacting group and a mercaptan group. Modification may be carried out by either partially esterifying the resin with a mercapto alcohol, (e.g., see U.K. patent No. 937,072) or by partially neutralizing the resin with an alkyl mercaptoamine such as thioethanolamine, (e.g., see Belgian Patent No. 589,727 and U.K. Patent No. 1,183,564), precursors of alkyl mercaptoamines such as thiazolidines, e.g., see U.K. Patent No. 1,361,430, cyclomercaptoamines and mercaptoaminocarboxylic acids, as well as thiazolidine precursors of the latter. Suitably from 2 to 25%, preferably from 5 to 20%, of the acidic groups are modified. As an alternative to such modification, the reaction may be carried out in the presence of a dissolved sulphur compound as promotor; examples include alkyl mercaptans such as methyl and ethyl mercaptan and mercapto-substituted aliphatic carboxylic acids such as 3-mercaptopropionic acid.

The reactors may be filled with the aciues include adding the desired amount of dry resin, water-wet resin or a slurry of the resin to the reactor. The resin bed is suitably fixed and is usually supported on one or more grids.

Suitable phenols for use in the present invention should have a reactive hydrogen atom, preferably in the para-position relative to the phenolic hydroxyl group. Such phenols may be substituted by one or more alkyl groups, e.g., lower alkyl groups such as methyl or tertiary butyl groups; halogen atoms, such as chlorine atoms, or other non-interfering substituents. Specific examples of phenols include ortho- and meta-cresol; 2,6-dimethylphenol; ortho-sec.butylphenol; ortho-tert.butylphenol; 2,6-di-ter.butylphenol; 1,3,5-xylenol; tetramethylphenol; 2-methyl-6-tert.butylphenol; ortho-phenylphenol; ortho- and meta-chlorophenol; ortho-bromophenol; 6-chloro-ortho-cresol and 2,6-dichlorophenol. Phenol itself is the preferred phenol.

The carbonyl compounds used in the process may be aldehydes or ketones with the latter being preferred. Preferred ketones are those having at least one methyl group alpha to carbonyl group or are cyclic ketones. Specific examples include acetone, methyl ethyl ketone, methyl propyl ketone, acetophenone, methyl vinyl ketone and cyclohexanone. Acetone is the preferred ketone. The present invention is particularly suitable for the preparation of 2,2-bis(4-hydroxyphenyl)propane (Bisphenol A).

The molar ratio of phenol to carbonyl compound is at least 2 with a molar excess of phenol being preferred.

Suitable molar ratios are from 3:1 to 50:1, with molar ratios of from 10:1 to 30:1 being preferred. The optimum ratio depends inter alia on reaction conditions, e.g., temperature of reaction and desired conversion.

The reaction temperature in the reactors may vary between wide limits with reaction temperatures in the range of from 30° C. to 120° C. being suitable and reaction temperatures in the range of from 40° C. to 100° C. being preferred.

The reaction time may also vary between limits and depends inter alia on reaction temperature. For example an average total contact time of from 3 minutes to 10 hours may be used. The liquid hourly space velocity (LHSV) of the feedstream may vary between wide limits with velocities in the range of from 0.1 to 40 liters feedstream. liter catalyst$^{-1}$.hour$^{-1}$ being suitable.

The bisphenols so prepared may be used in a variety of applications such as to prepare anti-oxidants, epoxy resins and polycarbonate resins.

The process will now be illustrated by reference to the accompanying drawing which is a schematic diagram of a preferred embodiment of the present invention.

In this embodiment a feedstream 1, comprising the phenol and the carbonyl compound is continuously fed to reactor $A_1$ comprising a fixed bed of an acidic ion-exchange resin. A reactor $A_1$ effluent stream 2 is continuously withdrawn and divided into a stream 3 which is recycled to reactor $A_1$ and a further stream 4 which is continuously fed to a further reactor $A_2$ also comprising a fixed bed of an acidic ion-exchange resin. The reactor $A_2$ effluent stream 5 is continuously withdrawn and worked up to recover the bisphenol therefrom.

The following examples illustrate the instant process for preparing bisphenols and are for the purpose of illustration only and are in no way intended to limit the invention to the particular scheme illustrated. Modifications within the spirit and scope of the present invention will become apparent to these skilled in the art. Parts and percentages are by weight unless otherwise noted.

space hour velocity. The Bisphenol A was recovered from the second reactor effluent by the removal of acetone, water and a part of the phenol by distillation and the remaining phenol was removed by evaporation. The resulting diphenylolpropane (DPP) after 24 hours, and an ortho/para DPP to para/para DPP ratio of 2.3/97.7 and a color of 58 Hazen.

The first and second reactor effluents were analyzed periodically and the acetone conversions, on intake, determined. The results are presented in Table 1.

TABLE 1

| Run Hours | 10 | 20 | 40 | 80 | 160 | 320 | 640 |
|---|---|---|---|---|---|---|---|
| Acetone conversion in first reactor effluent (%) | 47.5 | 46.5 | 44.5 | 40.5 | 34 | 30 | 25 |
| Acetone conversion in second reactor effluent (%) | 61.5 | 61 | 59 | 57 | 53 | 49 | 44 |

EXAMPLE 2 TO 4

Example 1 was repeated with the difference that the first reactor effluent was divided into two streams. One stream (50%w) was recycled to the first reactor and the other stream (50%w), recycle ratio of 1:1, was fed to the second reactor. The liquid space hour velocities of the fresh feedstream and of the recycle stream to the first reactor were both 8.4 liter.liter catalyst$^{-1}$.hour$^{-1}$. The recovered diphenylol propane (DPP) had an ortho/para KPP to para/para KPP ratio of 2.3/97.7 and a color of 57 Hazen. The first and second reactor effluents were analyzed periodically and the acetone conversions, on intake, were determined. The results are presented in Table II.

The above example was repeated with the differences that a recycle ratio of 0.5:1 (Example 3) and a recycle ratio of 1.5:1 (Example 4) were used. The recovered DPP had the same properties. The acetone conversions, on intake, in the effluents are also given in Table II.

TABLE II

| Recycle Ratio | Example 3 0.5 : 1 | | | | Example 2 1 : 1 | | | | | | | Example 4 1.5 : 1 | | | |
|---|---|---|---|---|---|---|---|---|---|---|---|---|---|---|---|
| Run Hours | 10 | 80 | 160 | 320 | 10 | 20 | 40 | 80 | 160 | 320 | 640 | 10 | 80 | 160 | 320 |
| Acetone conversion in first reactor effluent (%) | 44 | 43 | 41 | 39 | 40 | 40 | 40 | 40 | 39 | 39 | 39 | 38 | 38 | 38 | 38 |
| Acetone conversion in second reactor effluent (%) | 58 | 57 | 56 | 54 | 54 | 54 | 54 | 54 | 54 | 54 | 54 | 52 | 52 | 52 | 52 |

EXAMPLE 1

Two tubular reactors (150 cm long; 2 cm internal diameter), connected in series, were each partially filled with an aqueous slurry containing 130 g (dry basis) of a sulphonated styrene/divinylbenzene acidic ion-exchange resin which had been partially neutralized (10%) with thioethanolamine having an exchange capacity of 4.25 meq H+/g of dry resin, and the water drained-off to form fixed beds of resin. Both reactors were maintained at a temperature of 65° C.

A feedstream comprising phenol and acetone (molar ratio of 15:1) was continuously passed through the first reactor at a liquid space hour velocity of 8.4 liter.liter catalyst$^{-1}$.hour$^{-1}$. and the effluent continuously withdrawn and fed to the second reactor at the same liquid

What we claim is:

1. A continuous process for the preparation of 2,2-bis(4-hydroxyphenyl)propane comprising reacting at a temperature from about 30° C. to about 120° C., at least two moles of phenol with acetone in the presence of an acidic ion-exchange resin having an exchange capacity of at least 2.0 meq H+/g of dry resin, in a reaction zone comprising at least two reactors in series and recovering the 2,2-bis(4-hydroxyphenyl)propane from the effluent from the last reactor, wherein a part of the effluent from at least one reactor, with the exception of the last reactor, is recycled.

2. The process of claim 1 wherein the effluent is recycled to at least the first reactor.

3. The process of claim 1 wherein the recycle ratio is in the range of from 0.1:1 to 10:1.

4. The process of claim 1 wherein the reaction zone comprises two reactors in series.

5. The process of claim 1 wherein the acidic ion-exchange resin is a sulphonated styrene-divinylbenzene copolymer.

6. The process of claim 1 wherein the molar ratio of phenol to acetone is from 10:1 to 30:1.

7. The process of claim 1 wherein the reaction temperature is from 40° C. to 100° C.

8. The process of claim 5 wherein the ion-exchange resin has been partially neutralized with an alkyl mercaptoamine.

* * * * *